United States Patent [19]
Hata et al.

[11] Patent Number: 5,654,009
[45] Date of Patent: Aug. 5, 1997

[54] DELAYED ACTION PREPARATION

[75] Inventors: Takehisa Hata, Nagaokakyo; Akira Kagayama, Ikoma; Sumihisa Kimura; Satoshi Ueda, both of Kawanishi; Saburo Murata, Takarazuka, all of Japan

[73] Assignee: Fujisawa Pharmaceutical Co., Ltd., Osaka, Japan

[21] Appl. No.: 635,556

[22] Filed: Apr. 22, 1996

Related U.S. Application Data

[62] Division of Ser. No. 320,787, Oct. 11, 1994, abandoned, which is a continuation of Ser. No. 117,164, filed as PCT/JP92/00318, Mar. 18, 1992, abandoned.

[30] Foreign Application Priority Data

Mar. 25, 1991 [JP] Japan ................... 3-132442

[51] Int. Cl.$^6$ ................... A61K 9/50
[52] U.S. Cl. ................... 424/490; 424/492; 424/496; 424/497

[58] Field of Search ................... 424/490, 491, 424/492, 493, 494, 497

[56] References Cited

U.S. PATENT DOCUMENTS

| | | | |
|---|---|---|---|
| 4,871,549 | 10/1989 | Ueda et al. | 424/494 |
| 5,061,492 | 10/1991 | Okada et al. | 424/423 |

*Primary Examiner*—Amy Hulina
*Attorney, Agent, or Firm*—Oblon, Spivak, McClelland, Maier & Neustadt, P.C.

[57] ABSTRACT

The invention relates to a delayed action preparation which comprises a core comprising a drug and a swelling agent and an outer membrane comprising a biodegradable high molecular weight substance characterized in that the swelling agent is contained in a sufficient amount to cause a explosion of the outer membrane of biodegradable high molecular weight substance at a definite time after administration. This preparation provides for free control over the timing of drug release and is suited for administration not only by the oral route but also by the intramuscular, subcutaneous and other routes.

21 Claims, No Drawings

DELAYED ACTION PREPARATION

This is a division of application Ser. No. 08/320,787 filed on Oct. 11, 1994, now abandoned which is a continuation of application Ser. No. 08/117,164, filed Sep. 17, 1993, now abandoned, filed as International PCT Application No. PCT/JP92/00318, on Mar. 18, 1992.

TECHNICAL FIELD

This invention relates to a delayed action preparation, which finds application in the field of medicine.

BACKGROUND ART

As a delayed action preparation providing for a lag time in the release of an active ingredient, the preparation comprising a drug, a swelling agent and a water-insoluble coating material and wherein said swelling agent is contained in a sufficient amount to explode an outer membrane of the water-insoluble coating material at a definite time after administration is disclosed in Japanese Patent Application Kokai S-62-30709.

Meanwhile, a microencapsulated dosage form comprising a core containing a drug and a drug reservoir therefor, such as gelatin, and a biodegradable high molecular weight substance as a coating material is known from Japanese Patent Publication S-60-100516.

The preparation described in Japanese Patent Publication Kokai S-62-30709 referred to above, the outer membrane of which is made of a water-insoluble coating material such as ethylcellulose has the disadvantage that the outer membrane which is not decomposed or solubilized in the body fluid remains in the body even after releasing the drug. Therefore, although the residual outer membrane substance is excreted from the body rather easily after oral administration, it is hardly excreted when the preparation is administered intramuscularly, subcutaneously or otherwise.

The preparation disclosed in Japanese Patent Publication Kokai S-60-100516 is disadvantageous in that because the volume of the drug reservoir is small, the outer membrane is not exploded and although the drug is released gradually with progressive decomposition of the outer membrane, the pattern and rate of drug release cannot be-freely controlled and, the release after a designed lag time cannot be expected.

DISCLOSURE OF INVENTION

The inventors of this invention found, after a serious research endeavor to overcome the above-mentioned disadvantages, that when a biodegradable high molecular weight substance is used as an outer membrane material and a swelling agent is contained in just a sufficient amount to explode the outer membrane after lapse of a predetermined time after administration in a core containing a drug to be released, a preparation is obtained which releases the drug with a predetermined lag time and the outer membrane of which is then gradually decomposed by physiological enzymes, etc., thus being suited for administration by the intramuscular, subcutaneous or other route. This invention has been developed on the basis of the above finding.

The delayed action preparation of this invention is a preparation which comprises a core comprising a drug and a swelling agent and an outer membrane comprising a biodegradable high molecular weight substance, characterized in that said swelling agent is contained in just a sufficient amount to explode said outer membrane of biodegradable high molecular weight substance after lapse of a predetermined time after administration. When this preparation is administered to a recipient, water penetrated through the outer membrane of biodegradable high molecular weight barrier substance causes an expansion of the hydrated swelling agent within the core to cause a explosion of the outer membrane, whereupon the drug is let out for the first time (a lag time in drug release is realized) and this release of the drug is followed by gradual decomposition of the outer membrane by physiological enzymes and the like.

The drugs which can be used in the delayed action preparation of this invention includes, among others, antitumor agents (e.g. bleomycin hydrochloride, mitomycin C, adriamycin, fluorouracil, tetrahydrofuryl-5-fluorouracil, cytarabine, etc.), physiologically active peptides (e.g. insulin, calcitonin, somatostatin, somatomedin, etc.), antibiotics (e.g. cefazolin, ceftizoxime, cefalotin, cefoperazone, etc.), antiulcer agents (e.g. cimetidine etc.) and antiinflammatory-analgesic agents (e.g. sodium diclofenac, etc.).

The swelling agent for use in the delayed action preparation of the invention includes, among others, disintegrators [for example, low-substituted hydroxypropylcellulose, calcium carboxymethylcellulose, Ac-Di-Sol (sodium carboxymethylcellulose, the trademark of F.M.C.), Explotab (sodium starch glycolate, the trademark of Edward Mendel), starch, agar, etc.], biodegradable high molecular weight substances, for example, polyacrylamide, polycarbonate, chitin, chitosan and its derivatives, gelatin, sodium hyaluronate, collagen, fibrinogen, albumin, polylactic acid, polyglycollic acid, poly(lactic acid-co-glycollic acid), etc.], synthetic polymers (for example, polyvinyl acetate, polyacrylic acid, acrylate copolymer, polyethylene glycol, etc.), inorganic salts (for example, magnesium chloride, calcium sulfate, etc.), organic salts (for example, sodium carbonate, calcium bicarbonate, etc.), sugars (for example, d-mannitol, sucrose, glucose, etc.), tartaric acid and urea. The low-substituted hydroxypropylcellulose mentioned above is a substituted cellulose as substituted by hydroxypropyl within the range of 5 to 16% by weight as hydroxypropoxy.

When the delayed action preparation of the invention is intended for administration by a non-oral route, e.g. intramuscular or subcutaneous administration, it is preferable to use, among the above-mentioned swelling agents, those species which are susceptible to decomposition by physiological enzymes etc., such as the biodegradable high molecular weight substances mentioned hereinbefore.

The coating material for use in the delayed action preparation of the invention is a biodegradable high molecular weight substance such as, for example, various polyesters [e.g. polylactic acid, polyglycollic acid, poly-e-caprolactone, poly(lactic acid-co-glycollic acid), poly-β-hydroxybutyric acid, polyhydroxyvaleric acid, polyhydroxybutyric acid-hydroxyvaleric acid copolymer, etc.], polycyanoacrytates, poly(amino acids), poly(ortho-esters) and polycarbonates.

The delayed action preparation of the invention includes beads and granules, among other forms.

For the manufacture of the delayed action preparation of the invention, beads or granules either coated with the drug or containing the drug are first prepared.

By way of illustration, nonpareil beads (microspheres of sucrose, manufactured by Freund Industries) are swirled in a centrifugal granulator or agitated in an air stream in a fluidized-bed granulator.

With a centrifugal granulator, the drug is deposited on the core beads with a spray-mist of a solution of a suitable binder (e.g. hydroxypropylmethylcellulose, methylcellulose, polyvinylpyrrolidone, sodium alginate, collagen, fibrinogen, sodium hyaluronate, etc.) in a solvent (e.g. water, ethanol, etc.).

When a fluidized-bed granulator is used, the drug is dissolved or suspended in a binder solution such as that mentioned above and the nonpareil cores are coated with the resulting solution or suspension.

As an alternative procedure, granules each containing the drug, an excipient (e.g. sucrose, lactose, mannitol, microcrytalline cellulose, etc.) and those additives which are conventionally used in the field are manufactured by the conventional pharmaceutical procedure.

The beads or granules carrying or containing the drug as prepared above are then coated with said swelling agent in the same manner as described above.

In the delayed action preparation of the invention, each of the drug layer and the swelling agent layer is not limited to single layer.

Thus, if necessary, a plurality of layers of the drug and of the swelling agent may be alternately deposited by the above-described procedure so as to achieve various patterns of drug release.

A further alternative technique for providing the delayed action preparation of the invention is as follows.

Using nonpareil beads as the cores, a mixture of the drug and swelling agent is deposited on the cores in the same manner as above.

As a still further alternative, core granules each containing the drug and swelling agent as well as the excipient and additives mentioned above are prepared by the conventional procedure.

Where gelatin or the like is used as the swelling agent, a solution of the drug in a warm aqueous solution of the swelling agent is dripped into a cooled oily medium [e.g. Panacete 810 (the trademark of Nippon Oils and Fats] and the mixture is washed free of the oily medium and dried to provide core granules containing the swelling agent and drug.

Where chitosan is used as the swelling agent, chitosan is dissolved in water in the presence of an acid (e.g. hydrochloric acid or glacial acetic acid) and this chitosan solution is dripped into a bath containing the drug and a base (e.g. sodium tripolyphosphate, sodium hydroxide, etc.) to coagulate chitosan to give core granules and the system is ripened for gradual saturation with the drug. Thereafter, the system is washed free of the base and dried to provide chitosan core granules containing the drug.

Finally the core granules containing the drug and swelling agent, as prepared by any of the above-described processes, are coated with a coating material containing a biodegradable high molecular weight substance and suitable additives (e.g. talc, polyethylene glycol, silicone, diethyl sebacate, titanium dioxide, etc.) by the conventional procedure.

By way of illustration, the above beads or granules are placed in a fluidized-bed granulator and, under agitation with an air stream, the respective particles are coated with a solution of said biodegradable high molecular weight substance in a suitable solvent (e.g. ethanol, dichloromethane, etc.) containing said additives, either dissolved or suspended.

The amount of the drug in the delayed action preparation of this invention, thus manufactured, is preferably 0.05 to 20% by weight but this range is not critical and can be broadened according to the dosage of the drug, for instance.

It is essential that the swelling agent should be contained in an amount just sufficient to cause a explosion of the outer membrane of biodegradable high molecular weight substance on hydration and expansion at a predetermined time after administration. The amount of the swelling agent in the delayed action preparation of the invention may generally range from 30 to 80% by weight but the actual amount should be selected with reference to the type of swelling agent, the type and amount of outer membrane substance and the required lag time.

The amount or coverage of the biodegradable high molecular weight substance is preferably 1 to 70% by weight but this range is not critical and can be adjusted according to the required lag time.

The preferred size of the delayed action preparation is 0.01 mm to 5 mm in diameter and specific preparations that can be provided include oral preparations, intramuscular injections, subcutaneous preparations, rectal suppositories, transnasal preparations, transpulmonary preparations and so on.

The following experimental data are typical evidence of the effectiveness of this invention.

Release Test 1

Test preparation 1: The preparation prepared in Example 1 which appears herein-after after [l-polylactic acid coverage of 24% by weight]

Test preparation 2: The preparation prepared in Example 1 [l-polylactic acid coverage of 49% by polylactic acid]

Test preparation 3: The core granule prepared in Example 1 [without l-polylactic acid coverage of]

Method Dissolution Test, Method II, of Japanese Pharmacopoeia XI (paddle method: physiological saline 900 ml, 37° C., 100 rpm)

Results The dissolution test data are shown in Table 1.

TABLE 1

| Test preparation | Release rate (%) | | | | | | |
|---|---|---|---|---|---|---|---|
| | 10 Min. | 30 Min. | 60 Min. | 90 Min. | 120 Min. | 180 Min. | 240 Min. |
| 1 | 0.0 | 1.4 | 28.0 | 58.5 | 81.8 | 96.6 | 100 |
| 2 | 0.0 | 0.2 | 9.0 | 28.1 | 53.3 | 88.9 | 100 |
| 3 | 89.2 | 100 | 100 | 100 | 100 | 100 | 100 |

Release test 2

Test preparation 4: The preparation prepared in Example 4 which appears herein-after [l-polylactic acid coverage of 43% by weight]

Test preparation 5: The preparation prepared in Example 4 [l-polylactic acid coverage of 58% by weight]

Test preparation 6: The core granule prepared in Example 4 [without l-polylactic acid coverage of]

Method Dissolution Test, Method II, of Japanese Pharmacopoeia XII [paddle method: distilled water 900 ml, 37° C., 100 rpm]

Results The dissolution test data are shown in Table 2.

TABLE 2

| Test Preparation | Release rate (%) | | | | | | | | | | | | |
|---|---|---|---|---|---|---|---|---|---|---|---|---|---|
| | 0.5 Hr. | 1 Hr. | 2 Hr. | 4 Hr. | 6 Hr. | 8 Hr. | 10 Hr. | 12 Hr. | 14 Hr. | 16 Hr. | 20 Hr. | 24 Hr. | 36 Hr. |
| 4 | 0 | 0 | 6.9 | 40.2 | 68.2 | 85.6 | 94.2 | 97.4 | 99.3 | 100 | — | — | — |
| 5 | 0 | 0 | 0 | 0 | 0 | 0 | 8.1 | 19.5 | 31.8 | 42.6 | 62.1 | 77.5 | 100 |
| 6 | 100 | — | — | — | — | — | — | — | — | — | — | — | — |

Bioavailability test

The above preparations 4 through 6 were respectively administered, in a dose of 10 mg (as cytarabine)/kg, subcutaneously at the back of male SD rats (b.wt. 230 g –270 g, n=3 for each dosage form). Blood sampling was serially carried out and the plasma concentration of cytarabine in each sample was determined by high-performance liquid chromatography.

| Test Preparation | Plasma cytarabine concentration (μg/ml) | | | | | | | | | | | | |
|---|---|---|---|---|---|---|---|---|---|---|---|---|---|
| | 0.5 Hr. | 1 Hr. | 2 Hr. | 4 Hr. | 6 Hr. | 8 Hr. | 10 Hr. | 12 Hr. | 14 Hr. | 16 Hr. | 20 Hr. | 24 Hr. | 36 Hr. |
| 4 | 0 | 0 | 0.1 | 0.9 | 1.6 | 1.5 | 1.2 | 0.7 | 0.4 | 0.2 | 0 | — | — |
| 5 | 0 | 0 | 0 | 0 | 0 | 0 | 0.4 | 1.4 | 1.5 | 1.5 | 1.2 | 0.9 | 0.1 |
| 6 | 4.0 | 6.4 | 4.1 | 1.3 | 0.3 | 0.1 | 0 | — | — | — | — | — | — |

(mean of 3 animals)

It is apparent from the above results of Release Tests 1 and 2 that, in the delayed action preparation of the invention, the drug begins to be released with a definite time lag and is completely released in a definite time and that this lag time can be freely controlled by adjusting the amount of biodegradable high molecular weight substance.

It is also clear from the results of the above bioavailability test that the delayed action preparation of this invention releases the drug with a definite time lag even in vivo to thereby maintain the blood concentration of the drug.

Therefore, the delayed action preparation of this invention offers the following advantages.

(1) The rate and pattern of drug release are indifferent to the inherent solubility and dissolution rate of the drug;
(2) the rate and pattern of drug release are not dependent on the pH of body fluid;
(3) the drug is completely released from the administered preparation;
(4) the lag time of drug release can be freely controlled by adjusting the type and amount of swelling agent and the type and amount of biodegradable high molecular weight substance used as the coating material in the preparation;
(5) a variety of release patterns (e.g. zero-order, repeat and other kinetics) can be obtained by using beads or granules with dissimilar lag times in a pertinent combination; and
(6) since the outer membrane is made of a biodegradable high molecular weight substance, the outer membrane is gradually decomposed after release of the drug and does not remain in the body so that the preparation can be utilized not only for oral administration but also for administration by other routes, e.g. intramuscular or subcutaneous administration.

The following examples are intended to describe the invention in further detail.

EXAMPLE 1

The powdery drug (0.6 g) was dissolved in a 15% aqueous solution of gelatin (400 ml) prewarmed to 60° C. and the solution was dripped from a 1.2 mm-diameter nozzle into a cooled coagulation bath containing Panacete 810 (2 l) to provide drug-containing gelatin beads about 4 mm in diameter. The beads were transferred into chlorofluorocarbon-11 (500 ml) for washing off Panacete 810 and dried to provide drug-containing gelatin beads about 2 mm in diameter.

Using a fluidized-bed granulator (Freund Industries), these core beads (20 g) were coated with a solution of l-polylactic acid (20 g) in ethanol-dichloromethane (2:3) (500 ml) to provide two delayed action preparations with l-polylactic acid coverages of 24% and 49% by weight.

EXAMPLE 2

Chitosan (20 g) was dispersed in distilled water (1 l) and after addition of glacial acetic acid (15 ml), the dispersion was stirred for 30 minutes to prepare a clear chitosan solution.

This solution was dripped from a 1.2 mm (dia.) nozzle into a coagulation bath prepared by dissolving the powdery drug (20 g) in 2% aqueous sodium tripolyphosphate (2 l) to provide chitosan beads about 4 mm in diameter. The system was gently stirred for 12 hours for saturation with the drug. The beads were then washed with methanol and dried to provide drug-containing chitosan beads about 1 mm in diameter.

Using a fluidized-bed granulator, the above core beads (10 g) were coated with a solution of l-polylactic acid (10 g) in ethanol-dichloromethane (2:3) (250 ml) to provide a delayed action preparation with a l-polylactic acid coverage of 29% by weight.

EXAMPLE 3

Using a fluidized-bed granulator, nonpareil beads (400 g), 350 to 500 μm in diameter, were coated with a solution of the powdery drug (8 g) in 0.1% aqueous sodium hyaluronate (400 ml).

Using a centrifugal granulator (Freund Industries), the above drug-coated granules (400 g) were further spray-coated with a solution of sodium hyaluronate (600 g), i.e. a swelling agent, in 60% ethanol.

The granules (20 g) thus obtained were coated with a solution of l-polylactic acid (20 g) in ethanol-dichloromethane (2:3) (500 ml) in a fluidized-bed granulator to provide a delayed action preparation with a l-polylactid acid coverage of 40% by weight.

EXAMPLE 4

A solution of cytarabine (5 g) in a 20% aqueous solution of gelatin prewarmed to 60° C. (520 ml) was dripped from a 1 mm (dia.) nozzle into a cooled coagulation bath of Pahacete 810 (2 l) to provide cytarabine-containing gelatin beads about 3 mm in diameter.

After drying, the beads were transferred into chlorofluorocarbon-11 (1 l) for washing off Panacete 810 and dried again to provide 5% cytarabine-containing gelatin beads 1.8 mm in diameter.

Using a fluidized-bed granulator, these core beads (50 g) were coated with a solution of l-polylactic acid (100 g) in ethanol-dichloromethane (3:4) (2 l) to provide two delayed action preparations with l-polylactic acid coverages of 43% and 58% by weight.

EXAMPLE 5

The cytarabine-containing gelatin core beads prepared in Example 4 (20 g) were coated with a solution of poly(dl-lactic acid-co-glycollic acid) (20 g) in chloroform (600 g) in a fluidized-bed granulator to provide a delayed action preparation.

EXAMPLE 6

The cytarabine-containing gelatin core beads obtained in Example 4 (30 g) were coated with a solution of poly-β-hydroxybutyric acid (30 g) in chloroform (1960 g) in a fluidized-bed granulator to provide a delayed action preparation.

EXAMPLE 7

Chitosan (20 g) was dispersed in distilled water (1 l) and after addition of glacial acetic acid (15 ml), the dispersion was stirred for 30 minutes to give a clear chitosan solution. This solution was dripped from a 1.2 mm (dia.) nozzle into a coagulation bath prepared by dissolving cytarabine (10 g) in 2% aqueous sodium tripolyphosphate (2 l) to provide chitosan beads about 4 mm in diameter. The system was gently stirred for 16 hours for saturation with the drug. Then, the beads were washed with methanol and dried to provide cytarabine-containing chitosan beads about 1 mm in diameter.

These core beads (10 g) were coated with a solution of l-polylactic acid (10 g) in ethanol-dichloromethane (2:3) (250 ml) in a fluidized-bed granulator to provide a delayed action preparation.

EXAMPLE 8

Using a centrifugal granulator, nonpareil beads (800 g), 350–500 μm in diameter, were coated with a solution of fluorouracil (10 g) in a 0.01% solution of sodium hyaluronate in 60% ethanol (2 l).

Then, in the centrifugal granulator, the above fluorouracil-coated beads (400 g) were further spray-coated with a solution of sodium hyaluronate (600 g), a swelling agent, in 60% ethanol.

Using the resulting beads as cores (20 g), a solution of l-polylactic acid in ethanol-dichloromethane (2:3) (500 ml) was coated to provide a delayed action preparation.

We claim:

1. A method for the controlled administration of a drug to a mammal in need thereof, comprising the step of:

intramuscularly or subcutaneously administering a delayed action preparation comprising a core portion containing a drug and a hydratable swelling agent, and an outer membrane surrounding said core portion, said outer membrane comprising 1–70% by weight of the preparation of a biodegradable high molecular weight substance, wherein said hydratable swelling agent is selected from the group consisting of polyacrylamide, polycarbonate, chitin, chitosan, gelatin, sodium hyaluronate, collagen, fibrinogen, polylactic acid, polyglycolic acid and poly(lactic acid-co-glycolic acid), is present in an amount of 30–80% by weight of said preparation and said amount is sufficient to rupture said outer membrane when said hydratable swelling agent is hydrated by penetration of water through said outer membrane after administration intramuscularly or subcutaneously causing initial release of said drug through said outer membrane.

2. The method of claim 1, wherein said administering is intramuscularly administering.

3. The method of claim 1, wherein said administering is subcutaneously administering.

4. The method of claim 1, wherein said hydratable swelling agent is polyacrylamide.

5. The method of claim 1, wherein said hydratable swelling agent is polycarbonate.

6. The method of claim 1, wherein said hydratable swelling agent is chitin.

7. The method of claim 1, wherein said hydratable swelling agent is chitosan.

8. The method of claim 1, wherein said hydratable swelling agent is gelatin.

9. The method of claim 1, wherein said hydratable swelling agent is sodium hyaluronate.

10. The method of claim 1, wherein said hydratable swelling agent is collagen.

11. The method of claim 1, wherein said hydratable swelling agent is fibrinogen.

12. The method of claim 1, wherein said hydratable swelling agent is polylactic acid.

13. The method of claim 1, wherein said hydratable swelling agent is polyglycolic acid.

14. The method of claim 1, wherein said hydratable swelling agent is poly(lactic acid-co-glycolic acid).

15. The method of claim 1, wherein said delayed action preparation has a diameter of 0.01 mm to 5 mm.

16. The method of claim 1, wherein said initial release of said drug through said outer membrane occurs after a lag time period.

17. The method of claim 16, wherein said lag time period is 10–60 minutes.

18. The method of claim 1, wherein said delayed action preparation comprises 1–70% by weight of said biodegradable high molecular weight substance.

19. The method of claim 7, wherein the biodegradable high molecular weight substance is selected from the group consisting of polylactic acid, polyglycolic acid, poly-ε-caprolactone, poly(lactic acid-co-glycolic acid), poly-β-hydroxybutyric acid, polyhydroxyvaleric acid, polyhydroxybutyric acid-hydroxyvaleric acid copolymer, polycyanoacrylates, poly(amino acids), poly(ortho-esters) and polycarbonates.

20. The method of claim 8, wherein the biodegradable high molecular weight substance is selected from the group consisting of polylactic acid, polyglycolic acid, poly-ε-caprolactone, poly(lactic acid-co-glycolic acid), poly-β-hydroxybutyric acid, polyhydroxyvaleric acid, polyhydroxybutyric acid-hydroxyvaleric acid copolymer, polycyanoacrylates, poly(amino acids), poly(ortho-esters) and polycarbonates.

21. The method of claim 9, wherein the biodegradable high molecular weight substance is selected from the group consisting of polylactic acid, polyglycolic acid, poly-ε-caprolactone, poly(lactic acid-co-glycolic acid), poly-β-hydroxybutyric acid, polyhydroxyvaleric acid, polyhydroxybutyric acid-hydroxyvaleric acid copolymer, polycyanoacrylates, poly(amino acids), poly(ortho-esters) and polycarbonates.

* * * * *